United States Patent
Gauglitz et al.

(10) Patent No.: US 8,174,708 B2
(45) Date of Patent: May 8, 2012

(54) ANALYSIS OF MOLECULAR INTERACTIONS ON AND/OR IN THIN LAYERS

(75) Inventors: Guenter Gauglitz, Tuebingen (DE); Guenther Proll, Denkendorf (DE); Florian Proell, Rottenburg (DE); Lutz Steinle, Oberteuringen (DE); Markus Schubert, Tuebingen (DE)

(73) Assignee: Biametrics Maken und Rechte GmbH, Tuebingen (DE)

( * ) Notice: Subject to any disclaimer, the term of this patent is extended or adjusted under 35 U.S.C. 154(b) by 176 days.

(21) Appl. No.: 12/672,535

(22) PCT Filed: Aug. 9, 2008

(86) PCT No.: PCT/EP2008/006587
§ 371 (c)(1),
(2), (4) Date: May 13, 2010

(87) PCT Pub. No.: WO2009/019043
PCT Pub. Date: Feb. 12, 2009

(65) Prior Publication Data
US 2011/0026034 A1    Feb. 3, 2011

(30) Foreign Application Priority Data
Aug. 9, 2007   (DE) .......................... 10 2007 038 797

(51) Int. Cl.
G01B 11/02    (2006.01)
(52) U.S. Cl. ........................................ 356/630; 356/503
(58) Field of Classification Search .................. 356/503, 356/504, 630, 632
See application file for complete search history.

(56) References Cited

U.S. PATENT DOCUMENTS

| | | | |
|---|---|---|---|
| 6,867,420 B2 | 3/2005 | Mathies | 250/458 |
| 7,510,885 B2 | 3/2009 | Halls | 438/22 |
| 2006/0197960 A1 | 9/2006 | Bazylenko | 356/491 |
| 2009/0189515 A1 | 7/2009 | Halls | 313/504 |
| 2011/0026034 A1* | 2/2011 | Gauglitz et al. | 356/451 |
| 2011/0261191 A1* | 10/2011 | Byren et al. | 348/135 |

FOREIGN PATENT DOCUMENTS

| | | |
|---|---|---|
| DE | 19830727 | 1/1999 |
| DE | 102005015030 | 4/2006 |

OTHER PUBLICATIONS

"Photons and photonics in solar cells and photodiodes" J. Koehler et al, Themenheft Forschung, No. 2, 2005, p. 96-103.
"An Amorphous SiC/Si Two-Color Detector" H. Tsai et al, IEEE Electron Device Letters, vol. EDL-5, No. 8 Aug. 1987.

* cited by examiner

Primary Examiner — Patrick J Connolly
(74) Attorney, Agent, or Firm — Jonathan Myers; Andrew Wilford

(57) ABSTRACT

The invention relates to a carrier for a thin layer and a method for the analysis of molecular interactions on and/or in such a thin layer. A thin layer disposed on a carrier is illuminated with electromagnetic radiation from at least one radiation source and a reflected radiation part on boundary surfaces of the thin layer is detected by means of an optoelectronic converter that converts the detected radiation into a frequency- and intensity-dependant photocurrent. A reading voltage is applied to the optoelectronic converter. By changing the reading voltage, the spectral sensitivity of the optoelectronic converter is varied such that a substantially constant photocurrent is obtained. Alternatively or in addition to varying the spectral sensitivity by changing the reading voltage, the reflected radiation part is detected with an optoelectronic converter that is designed as a sensor layer in the carrier. The carrier is particularly characterized in that it comprises a substrate on which at least one sensor layer with optoelectronic properties is disposed.

19 Claims, 6 Drawing Sheets

Fig. 1 - Prior Art

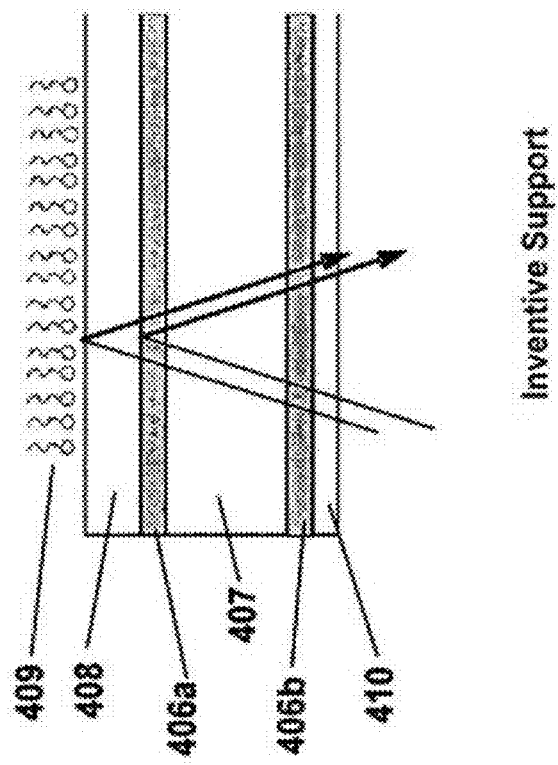
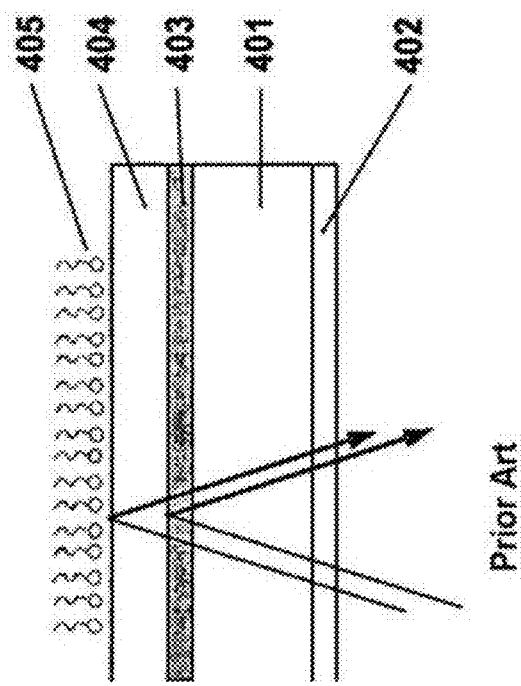

ANALYSIS OF MOLECULAR INTERACTIONS ON AND/OR IN THIN LAYERS

CROSS REFERENCE TO RELATED APPLICATIONS

This application is the US national phase of PCT application PCT/EP2008/006587, filed 9 Aug. 2008, published 12 Feb. 2009 as WO2009/019043, and claiming the priority of German patent application 102007038797.2 itself filed 9 Aug. 2007, whose entire disclosures are herewith incorporated by reference.

The invention relates to a support for a thin layer and a method of the examination of molecular interactions on and/or in such a thin layer.

Interactions of biologically active molecules take on a central role in biochemical processes. Examples are gene expression, signal transmission by hormones or neurotransmitters, immune defense by antigen antibody binding, or enzyme reactions. Each of these processes is preceded by the specific binding of a ligand to a biological receptor. The detection and characterization of such binding events are of critical importance in the description and understanding of the mechanisms and function of biochemical processes.

Common methods for characterizing biomolecular detection reactions are mostly based on a radioactive marking or fluorescence marking of one of the two binding partners. A disadvantage of these methods is that the marking process is associated with extensive and time-consuming purification of the binding partners, and the yield of the full biological function thereof cannot be guaranteed. Therefore, various methods for detecting marker-free biomolecular interactions have been analyzed on solid phases during the last few years, and suitable detection techniques have been developed that allow the direct observation of binding events on the surfaces and thus allow access to the thermodynamic and kinetic characterization of affinity reactions.

In particular, methods based on the reflectometric interference spectroscopy (RIfS) are suitable for marker-free detection. This optical detection method uses multiple reflection of electromagnetic radiation on thin transparent layers. Incident electromagnetic radiation is partially reflected on the outer faces (phase boundaries) of the layers due to different refractive indices. The superposition of the reflected radiation creates a characteristic interference pattern (A. Brecht, G. Gauglitz, W. Nahm, Analysis 20 (1992) 135; A. Brecht, G. Gauglitz, G. Kraus, W. Nahm, Sens. Actuators 11B (1993) 21; Brecht et al., Optical probes and converters, Biosensors & Bioelectron. 10 (1995), 923-936; Schmitt et al., An integrated system for optical biomolecular interaction analysis, Biosensors & Bioelectron. 12 (1997), 809-816). The modification of the optical layer thickness of the thin is layer analyzed, which may be connected, for example, with the agglomeration or the binding of molecules, causes a displacement of the interferogram. This displacement may be measured with respective to time. RIfS is therefore superbly suited, for example, for analyzing binding events on a surface.

A method suitable for analyzing physical, chemical, and/or biochemical reactions and interactions based on this principle is known, for example, from DE 198 30 727. However, the action described therein requires special optically coated supports. Furthermore, the method described is relative extensive in handling, and often delivers a relatively bad signal/noise ratio.

DE 10 2005 015 030 describes an RIfS method where the thin layer to be measured is irradiated with light from a light source and the radiation reflected onto the outer faces of the thin layer is measured on a detector, targeted measures being taken such that only monochromatic light of a single wavelength (or of a very narrow spectrum) reaches the detector. This is achieved in particular in that the light source used irradiates monochromatic light. Significant improvement of the signal/noise ratio may be obtained with the use of extremely narrow-band lasers and the selection of a suitable wavelength. However, a very unfavorable cost/use ratio must be accepted, as the devices required for carrying out the method are very expensive. Furthermore, layers having a predetermined layer thickness must be provided, which has also proven very disadvantageous in practice.

The object of the present invention is therefore to provide a method of analyzing molecular interactions that is not dependent upon predetermined analysis conditions and is also particularly cost effective. Furthermore, the novel method is to be superior to the solutions known from prior art, in particular with regard to the signal/noise ratio that can be achieved. The present invention further has the object of providing a support suitable for such a method.

The object is basically attained by a method of analyzing molecular interactions on and/or in at least one thin layer, comprising multiple steps. In a first step the thin layer is illuminated using electromagnetic radiation from at least one radiation source. The thin layer has outer faces on which the electromagnetic radiation may be reflected. The outer faces are preferably substantially planar and in particular are parallel to each other. In a further step of the method according to the invention at least one part of the radiation reflected onto the outer faces of the thin layer is detected by at least one optoelectronic sensor that converts the detected radiation into a frequency and intensity dependent photocurrent. In order to measure the photocurrent a reading voltage is applied to the optoelectronic sensor. The spectral sensitivity of the optoelectronic sensor is varied by modifying the reading voltage such that a substantially constant photocurrent is obtained (this process is hereinafter also called null balance).

Parameters may subsequently be derived from the reading voltage that characterize the interactions to be analyzed on and/or in the thin layer.

Contrary to methods known from the prior art and according to the invention, parameters are preferably not obtained directly from a modification of a photocurrent. Instead it is preferred to keep the photocurrent constant by variation of the reading voltage applied. Any changes to the layer thickness usually lead to a displacement of the edge of the interference spectrum beyond the detection curve and to changes in the intensity of the detector signal. According to the invention the inflection point of the sinusoidal detection curve may be displaced toward the inflection point of the interference spectrum by changing the reading voltage. Therefore, contrary to the known methods, the initial layer thickness no longer needs to be determined at the beginning of the analysis. Furthermore, the action according to the invention allows precise reactions to minute changes of the radiation intensity, and thus of the photocurrent. The measurement of current and the voltage default may be carried out in a more precise manner such that the signal/noise ratio is substantially improved in this manner. Any null balance may be carried out comparatively much more accurately than the extraction of an absolute photocurrent signal from background noise.

The thin layer being illuminated by the electromagnetic radiation is preferably on a fixed support according to a particularly preferred embodiment of the method according to the invention. The support may be, for example, a planar substrate of glass, plastic, or metal.

The thin layer on the support may be aligned to face incident radiation, or face away from it. In the latter case the support material must be at least partially permeable to the electromagnetic radiation used. Preferably, the illumination of the thin layer is carried out through the support.

The term "thin layer" in this context in particular means a layer whose thickness is between 0.1 nm and 100 μm. The layer thickness and optionally also the layer thickness during the method according to the invention may vary within this range.

The thin layer is preferably an optionally multilayer coating of organic molecules. Preferably the thin layer comprises at least one layer of molecules immobilized on the support. In other words, the support has a surface that is modified by molecules present on itself. The properties of the surface are determined by the characteristics of the immobilized molecules.

The molecular interactions to be analyzed are preferably physical, chemical, and/or biochemical reaction, detection, binding, and/or agglomeration events. The molecular interactions to be analyzed are in particular interactions between the immobilized molecules on the surface of the support and molecules from a sample (in short: sample molecules) that are brought into contact with the thin layer before and/or during the illumination. For this purpose the sample is preferably incubated in a flow cell (alternatively: in a stopped flow apparatus) with the immobilized molecules of the support. The sample is in particular a gaseous or a liquid sample.

Preferably none of the interaction partners have a is fluorescence marking or the like. The method according to the invention is preferably a method free of markers.

The immobilized molecules on the support are preferably at least partially molecules that are functionalized such that the sample molecules may bind to it via a covalent bond and/or in a noncovalent manner by an affinity reaction, or may agglomerate on it. Molecules suited for this purpose are known to the person skilled in the art. The molecules immobilized on the surface of the support may comprise, for example, amino, thiol, and carboxyl groups. In particularly preferred embodiments the surface having the immobilized molecules is made such that biological macro-molecules, such as proteins, peptides, nucleic acids, lipids, and carbohydrates may agglomerate as the sample molecules.

If the sample molecules are compatible with the molecules immobilized on the support, i.e. at least temporarily agglomerate thereon or may even form a covalent bond thereto, the layer thickness and/or the layer density may change as a function of the quantity and type of agglomerated molecules. In these cases the thin layer also comprises sample molecules in addition to the molecules immobilized on the support, which are now at least temporarily "immobilized" on their part.

The invention determines the change in thickness of the thin layer connected to such a binding or agglomeration event. If the layer thickness changes, the distance between the periphery of the thin layer facing the incident radiation and the periphery of the thin layer turned away from it also changes. The above-mentioned displacement of the interferogram created by is superimposition of the reflected electromagnetic radiation results from the associated optical path difference. The respective correlations are graphically illustrated in FIG. 1.

A thin layer may have two or more layers of immobilized molecules. In preferred embodiments a thin layer has at least one first layer of the functionalized molecules mentioned above to which sample molecules may bind via a covalent bond or in a noncovalent manner and at least one further layer of molecules between the first layer and the support. The at least one further layer may serve, for example, for better adhesion of the thin layer onto the support or for changing the optical properties of the layer system.

The electromagnetic radiation is preferably guided onto the thin layer via coupling elements. These preferably include lenses, lens systems, mirrors, or light guides such as fiber-optic waveguides. Also, instead of using coupling elements, appropriate free ray superstructures may also be realized.

According to the invention at least one punctiform or planar area of the thin layer is illuminated. During the measurement the thin layer may be positioned either perpendicular or at an angle smaller than 90° to the incident light radiation.

Generally, white light may be used as at least one radiation source. Preferably, however, the electromagnetic radiation is adjusted to the layer thickness changes to be expected.

In particularly preferred embodiments of the method according to the invention, the thin layer is illuminated using electromagnetic radiation having a spectral bandwidth of between 5 nm and 50 nm, in particular between 30 nm and 50 nm. In particular light diodes (LEDs), laser diodes, and/or lasers are suitable as the at least one radiation source for light of this bandwidth. Generally, a white light source may, of course, also be used, with a monochromator connected downstream of it.

Preferably the radiation using electromagnetic radiation occurs from the wavelength range of between 200 nm and 1500 nm.

An optoelectronic sensor according to the present invention is capable of converting light into a measurable variable, in fact into electric current.

According to the invention the optoelectronic sensor comprises a photodiode in a particularly preferred manner, in particular a diode of the a p-i-n, a p-n, a n-i-p-i-n type, and/or a Schottky diode.

Diodes of the p-i-n type are known to the person skilled in the art. Contrary to diodes of the p-n type the p-doped layer is not in direct contact with the n-doped layer, but instead a weakly doped or non-doped i-layer is positioned between them.

Schottky diodes also differ from common diodes of the p-n type in terms of their structure. Contrary to the p-n transition of a normal diode, a Schottky diode is formed by a semiconductor/metal transition that also has rectifying properties. Reference is made to pertinent literature with regard to detailed explanations.

As mentioned above the spectral sensitivity of the optoelectronic sensor may be varied by changing the reading voltage. This is preferably carried out via control means that detect the photocurrent generated by the optoelectronic sensor and optionally increase or reduce the voltage applied to the optoelectronic sensor, Suitable control means are known to the person skilled in the art.

In a method according to the invention an optoelectronic sensor may generally be used that is part of an external detector system that is used as a separate component in a structure for carrying out RIfS analyses.

However, according to the invention the reflected portion of the radiation may in particular also be detected by an optoelectronic sensor that may be a sensor layer in and/or on the above-mentioned support and carrying the thin layer to be analyzed. The support therefore acts in this embodiment not only as a "support," but simultaneously as a detector. Accordingly, a separate detector is no longer necessary such that a very simple and very cost-effective execution of RIfS analyses is enabled by this measure. Also, the optical efficiency of the method is improved by this measure by magnitudes, in particular since a detection optical path toward a separate detector may be omitted.

In a particularly preferred manner the optoelectronic sensor is a thin layer photodetector. The sensor layer in these embodiments usually comprises a thickness of not more than 10 μm. Detailed explanations as to the exact structure of a support acting as a detector follow below.

The method according to the invention may be employed in a versatile manner, and may in particular also be adjusted to specific detection tasks. In this manner the sensitivity of the method may, for example, be specifically varied in that the illumination spectrum and the spectral sensitivity of the optoelectronic sensor are displaced synchronously or in the opposite direction of larger or smaller wavelengths (for example, the illumination spectrum may be specifically varied by activation of the current in the opposite direction of multiple spectrally overlapping light diodes). For example, the illumination spectrum may also initially be shifted toward a fixed value in order to maximize the signal in order to then carry out a null balance by varying the reading voltage.

A support acting as a detector for a thin layer to be tested by RIfS is currently not yet known according to prior art. Accordingly, such a support or detector is the object of the present invention.

The above-stated object is therefore also attained by a support serving for analyzing molecular interactions on and/or in a thin layer and that may in particular be used in the method according to the invention in accordance with one of the embodiments thereof. In general, the support comprises a substrate on which at least one sensor layer having optoelectronic properties is provided. The support according to the invention has multiple layers in the following order of initially a protective layer, in particular of silicon dioxide, optionally a highly refracting layer, for example a layer of a highly refracting material, is preferably tantalum pentoxide or niobium pentoxide, and a substrate of glass, plastic or metal on which the at least one sensor layer having optoelectronic properties is provided.

For this purpose the thickness of the sensor layer is within a range of between 0.1 μm and 50 μm, in particular between 0.1 μm and 10 μm.

Within the scope of the method according to the invention the sensor layer may act as an optoelectronic sensor.

Like the above definition of the optoelectronic sensor, the term "optoelectronic properties" as used herein should be understood as the capacity of converting light into electric current.

A surface of the support according to the invention comprises a thin, optionally multilayered layer of organic molecules as have been described above. In a particularly preferred manner the support has a layer of immobilized organic molecules on its surface to which sample molecules may bind directly or after chemical modification via a covalent or noncovalent bond.

The thin layer to be analyzed is preferably placed on the protective layer of the support according to the invention. Optionally the protective layer forms the surface on which the support according to the invention comprises the thin layer of organic molecules.

The composition of the substrate is not relatively critical. For example, it may consist of glass, plastic, or of metal. Preferably, it is at least partially permeable to electromagnetic radiation, in particular radiation within a range of between 200 nm and 1500 nm.

Preferably, the sensor layer comprises at least one semiconductor material having optoelectronic properties. It same is preferably either amorphous, nanocrystalline, or polycrystalline. If it is nanocrystalline, it has in particular crystallites of sizes ranging between 1 nm and 100 nm. If it is a polycrystalline, it may have crystallites ranging in sizes of up to 100 μm.

It is in particular preferred that the sensor layer is at least partially based on silicon.

It is further preferred that the at least one sensor layer has a preferably permeable layer of at least one semiconductor material.

In further preferred embodiments the support according to the invention has at least one sensor layer comprising at least one layer subdivided into sections and made from at least one semiconductor material. In the sections of this layer the semiconductor material is present preferably in the form of individual strips or ribs, in particular running parallel to each other and preferably forming a uniform pattern.

Preferably, the layer that is preferably continuous and/or subdivided into sections of the at least one semiconductor material is a p-i-n (or vice-versa, for example n-i-p), p-n, a n-i-p-i-n type, and/or a Schottky diode.

In a particularly preferred manner the continuous and/or subdivided layer of the at least one semiconductor material has a sequence of sublayers comprising a varying optical bandgap, in particular of p-i-n, multiple i-sublayer, such as p-$i_1$-$i_2$-n, p-$i_1$-$i_2$-$i_3$-n, n-$i_1$-$i_2$-$i_3$-p, or n-$i_1$-$i_2$-p (or vice-versa) sequences.

Sequences of the n-i-p-i-n or p-i-n-i-p type may also be preferred, again both comprising one or multiple i-sublayers, such as n-$i_1$-p-$i_2$-$i_3$-n.

Such a structure ensures good controllability of the spectral sensitivity of the sensor layer.

The optical bandgap of the sublayers may be varied very easily by blending suitable elements. In some preferred embodiments at least one of the sublayers is blended with carbon at a varying optical bandgap for widening the bandgap. In other preferred embodiments at least one of the sublayers is blended with germanium at a varying optical bandgap for reducing the bandgap.

The sublayers are preferably substantially nanocrystalline, amorphous, or polycrystalline. In particular amorphous sublayers may, for example, be created from thermal separation of silicon from the gas phase. Usually, they have a low hydrogen content that is incorporated into the sublayer.

According to a particularly preferred embodiment the at least one, preferably continuous and/or subdivided layer of the semiconductor material of a support according to the invention has the following sequence of sublayers:
   a p-conducting Si:H layer
   a self-conducting Si:H layer
   a self-conducting Si:H layer
   a n-conducting Si:H layer,
where Si:H denotes a thin layer semiconductor on the basis of silicon that is amorphous or crystalline, preferably nanocrystalline, and/or undoped or doped and/or not blended, or blended with elements preferably selected from carbon (C), nitrogen (N), or germanium (Ge).

For example all of these sublayers are either amorphous ("a") or crystalline, preferably nanocrystalline ("nc"), and have some hydrogen ("H").

These properties—amorphous or crystalline, or nanocrystalline, undoped or doped, not blended or blended with elements preferably, but not exclusively selected from carbon, nitrogen, or germanium—may each be present in any combination as a characteristic profile of the thin layer semiconductor "Si:H." For example, amorphous SiGe, undoped, or a microcrystalline n-type doped silicon may be present, these examples being merely exemplary and not intended to limit any further possible combinations.

According to a particularly preferred embodiment at least the p-conducting layer and the adjoining self-conducting layer each have a carbon alloy ("C").

In addition to the at least one preferably continuous and/or subdivided layer of the at least one semiconductor material, the sensor layer has at least one contact layer in preferred embodiments that preferably directly adjoins at least one of the preferably continuous and/or subdivided layers of the at least one semiconductor material.

The at least one contact layer may also be continuous and/or subdivided into sections. If the one contact layer is subdivided into sections, it will preferably have individual strips or ribs that are in particular parallel to each other, forming a preferably uniform pattern.

The at least one contact layer may in particular consist of ZnO, ITO (indium/tin/oxide) and/or of a metal, in particular aluminum.

Preferably, the sensor layer has a contact layer and a layer that is subdivided into sections, made from a semiconductor material, and in direct contact with it, the contact layer preferably completely overlapping the adjoining layer on at least one side. In this manner an undesired lateral coupling of light may be eliminated.

In preferred embodiments of the support according to the invention a contact layer is on both sides of a preferably continuous and/or subdivided layer of the at least one semiconductor material. Preferably, the two contact sides are not in direct contact with each other for this purpose such that they may act as electrodes via which a voltage, in particular the reading voltage mentioned above, may be applied to the layer of the at least one semiconductor material.

In particularly preferred embodiments a layer subdivided into sections from the at least one semiconductor material is between a first continuously embodied contact layer, and a second contact layer subdivided into sections. For this purpose the second contact layer and the layer of the at least one semiconductor material are preferably substantially congruent to each other.

It is preferred that the at least one sensor layer of the support according to the invention has the following layer sequence:
- a first contact layer, in particular of zinc oxide
- a preferably continuous and/or subdivided layer of the at least one semiconductor material with optoelectronic properties
- a second contact layer, in particular of aluminum.

An optional part of the support according to the invention is an anti-reflection coating that may be applied in particular as an outer layer to the side of the support turned toward the incident radiation.

Preferably, the at least one layer based on the at least one semiconductor material, the at least one contact layer, the at least one protective layer, and the anti-reflection coating are at least partially permeable for electromagnetic radiation, in particular for radiation with the range of between 200 nm and 1500 nm.

Further characteristics of the invention are obvious from the figures of the drawing in connection with the dependent claims.

For this purpose individual characteristics may be either alone or in multiple combinations with each other in an embodiment of the invention. The preferred embodiments described merely serve as explanations and for the better understanding of the invention, and are in no way intended as limiting.

DESCRIPTION OF THE FIGURES

FIG. 4 shows a comparison of a support known from the prior art for a thin layer and a support according to the invention for a thin layer and acting as a detector.

FIG. 1 illustrates the principle known from the prior art, which the invention is based on, according to which a binding event may be tracked via the optical analysis of a thin layer. The figure illustrates a support 101 on which a thin layer comprising a layer 103 of functional immobilized molecules and a further layer 102 of molecules between the layer 103 and the support 101 is disposed (schematically illustrated). The support 101 may consist of, for example, glass, plastic, or metal. The layer 102 in particular serves for the better adhesion of the thin layer to the support. Sample molecules 105 may bind to the functional immobilized molecules of the layer 103. Subsequently, the thickness of the thin layer grows; the distance from its upper face to the phase boundary between the thin layer and the support (or to the lower face of the thin layer) becomes greater. Light being radiated from the bottom is now also reflected on the outer face 104 after binding of the sample molecules 105. Since it has to travel over a long path toward the outer face 104, a displacement of the interferogram results, created by the superimposition of the reflected electromagnetic radiation (the dotted line corresponds to the (base) interference spectrum, the continuous line corresponding to the sinusoidal detection curve measured after agglomeration of the sample molecules 105. This displacement may be determined in a time-resolved manner, allowing conclusions as to the changes in layer thickness, thus to the interactions between the sample molecules 105 and the functional immobilized molecules in the layer 103. The course of a change in layer thickness is shown on the right in the diagram by way of example. Up to approximately 350 s an increase of the layer thickness is observed, subsequently a reduction. This corresponds to the typical course of a binding reaction of antibodies to be detected on antigens immobilized on a support, and their subsequent separation.

FIG. 2 shows an arrangement for a method according to the invention for analyzing a thin layer by RIfS measurement. The arrangement comprises a support 201 (known from the prior art) on which the thin layer 202 to be analyzed is disposed. It comprises a layer 202a of functional molecules that are immobilized on the surface of the support via a further layer 202b of polyethylene glycol molecules. Furthermore, it comprises a layer 202c of sample molecules that are bound or agglomerated to the functional molecules 202a. The support 201 comprises a substrate 203 of Corning glass, a layer 204 of highly refracting material (tantalum pentoxide), and a protective layer 205 of silicon dioxide forming the surface of the support 201, on which the thin layer 202 to be analyzed is applied. A radiation source 206 (on the left bottom) supplies the electromagnetic radiation necessary for the analysis that is conducted onto the thin layer 202 via a coupling element (a Y light guide) 207. A fraction of the radiation reflected on the outer faces of the thin layer is in turn supplied to a separate detector 208 via the Y light guide 207. A support according to the invention may be used as the detector 208. It comprises a sensor layer on the basis of an amorphous, Si-based semiconductor material having optoelectronic properties, and is capable of converting the reflected radiation into a photocurrent. The spectral sensitivity of the optoelectronic sensor may be varied by changing the reading voltage such that a substantially constant photocurrent is obtained. Parameters subsequently derived from the curve of the reading voltage characterize the interactions to be analyzed on and/or in the thin layer 202. As an alternative direct parameters may also be derived from the changes of the photocurrent, which allow conclusions to be drawn regarding changes in thickness of the thin layer 202 that have occurred, thus to interactions on and/or in the thin layer 202.

FIG. 3 shows an embodiment of a support 300 according to the invention for analyzing molecular interactions on and/or in a thin layer. The layers above the substrate 301 made from Corning glass correspond to the arrangement in FIG. 2, while the layers below the glass substrate 301 correspond to a sensor layer, as described above. The sensor layer comprises a layer 302 having optoelectronic properties based on a semiconductor material, a first contact layer 303 of zinc oxide, and a second contact layer 304 of aluminum. The layer 302 having optoelectronic properties has a sequence comprising a p-conducting a-SiC:H layer 302a, a self-conducting a-SiC:H layer 302b, a self-conducting a-Si:H layer 302c, and a non-conducting a-Si:H layer 302d. The total thickness of the sensor is approximately 0.5-3 µm.

FIG. 4 shows a comparison of a support known from the prior art of a thin layer with a support according to the invention acting as a detector for a thin layer. The support known from the prior art substantially corresponds to the support illustrated in FIG. 1. It has a glass substrate 401, an anti-reflection coating 402, a layer 403 of highly refracting material, and a protective layer 404 of silicon dioxide on which is a thin layer 405 to be analyzed. On the right side a support according to the invention is illustrated having a sensor layer 406 (optionally also two sensor layers) having optoelectronic properties. Like the support known from the prior art it also comprises a glass substrate 407 and a protective layer 408 of silicon dioxide on which is a thin is layer 409 to be analyzed. There is either an upper sensor layer 406a or a lower sensor layer 406b or such layers on both sides of the substrate 407. The anti-reflection coating 410 below the sensor layer 406b is optional. Due to the high refractive index thereof the sensor layer 406a may also simultaneously assume the function of the interference-reinforcing, highly refracting layer 403 in the arrangement known from the prior art, and replace it.

FIG. 5 schematically shows an embodiment of a sensor layer of a support according to the invention (cross-section). The sensor layer is located on a glass substrate 501. A semiconductor material having optoelectronic properties in the form of elongated strips 502 aligned parallel to each other and extending perpendicular to the image plane is on it. The strips are coplanar and form a layer in it that is subdivided into sections. The contacts 503, which are also in the form of strips extending perpendicular to the image plane, are between the strips 502 and the substrate 501. The contact strips are thus coplanar and form a layer in it that is subdivided into sections. The contacts 503 are substantially completely covered by the strips 502. They are connected via a common contact (not illustrated). The layer subdivided into sections made from the semiconductor material is coated with a continuous, preferably impermeable contact layer 504. For this purpose the layer 504 also covers the strips 502, in particular at the sides. The contact layer 504 and the contact strips 503 are not in direct contact with each other. A voltage, in particular a reading voltage, may be applied to the strips 502 made from the semiconductor material having optoelectronic properties via the contact layer 504 and the contact strips 503 (or via a common contact that is not illustrated) for carrying out the method according to the invention.

FIG. 6 schematically shows an arrangement for controlling a support according to the invention, in particular within the scope of the method according to the invention. A layer made from at least one semiconductor material formed as an n-i-p diode is between a contact layer of zinc oxide and a contact layer of aluminum. The contact layers may act as electrodes such that a reading voltage may be applied to the semiconductor material positioned between them. By varying the reading voltage, the spectral sensitivity of the optoelectronic sensor may be varied such that a substantially constant photocurrent is obtained.

Figure 1:
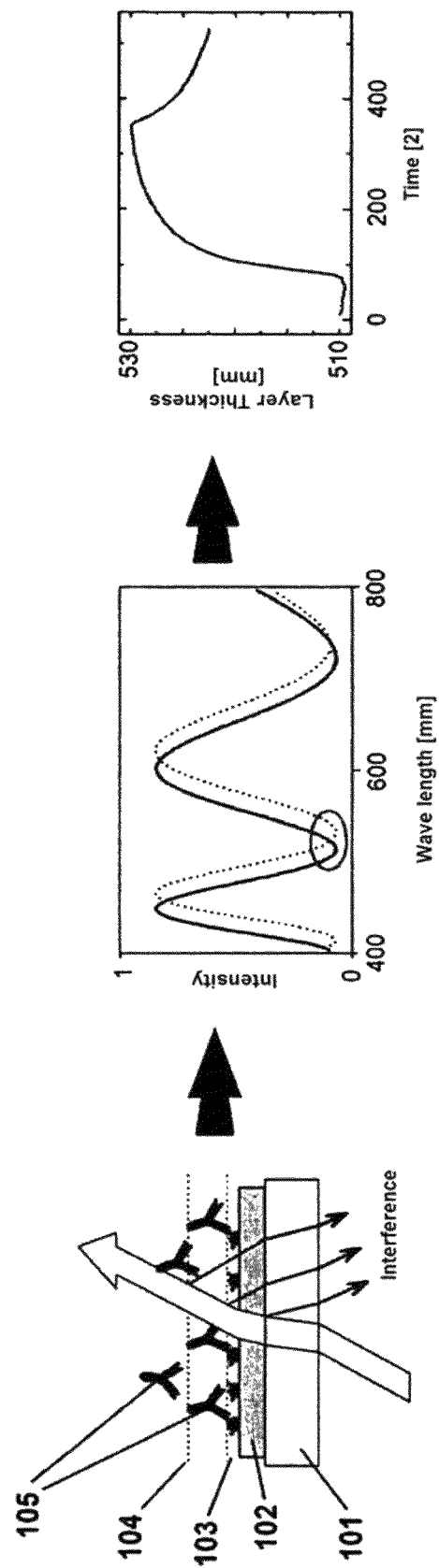
FIG. 1 shows the principle the invention is based on, according to which a binding event may be tracked via the optical analysis of a thin layer.
Figure 2:
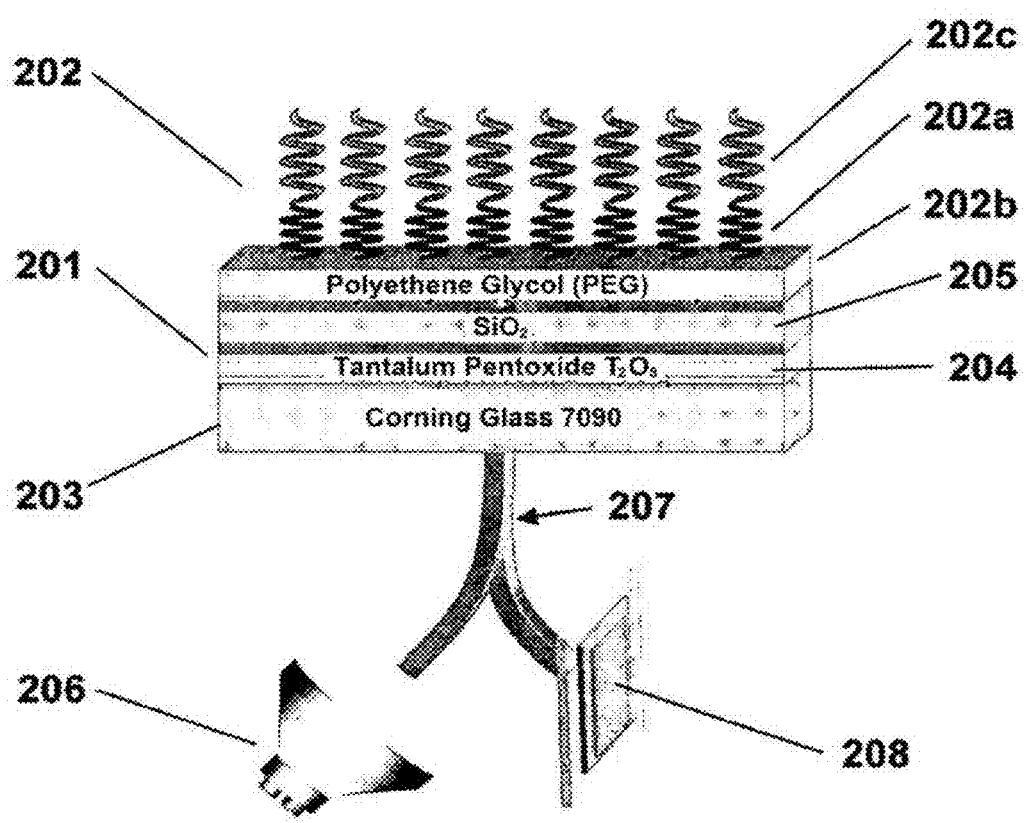
FIG. 2 shows an arrangement for a method according to the invention for analyzing a thin layer by an RIfS measurement, a support according to the invention being used as a separate detector.
Figure 3:
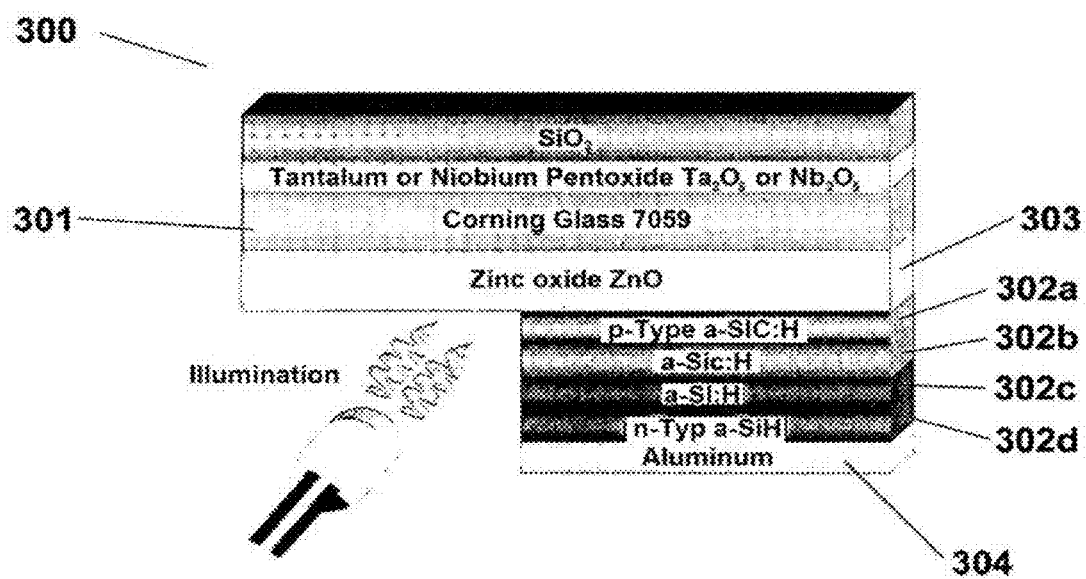
FIG. 3 shows an embodiment of a support according to the invention for analyzing molecular interactions on and/or in a thin layer.
Figure 5:
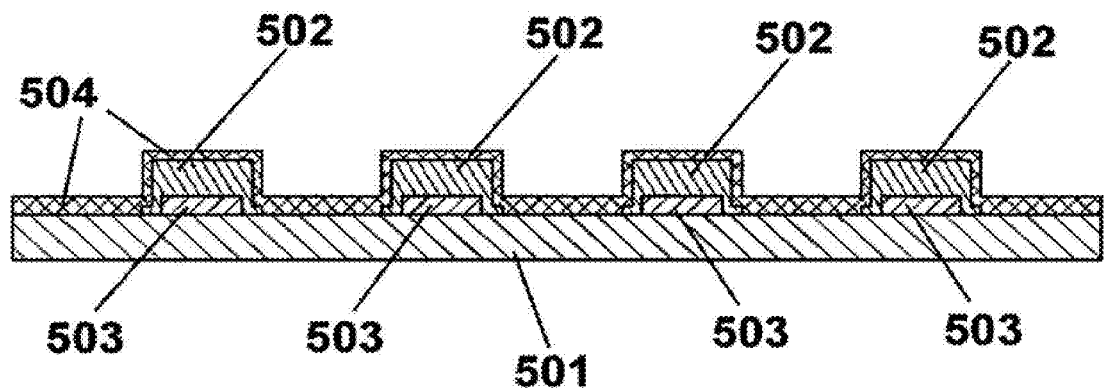
FIG. 5 shows an embodiment of a sensor layer of a support according to the invention (cross-section).
Figure 6:
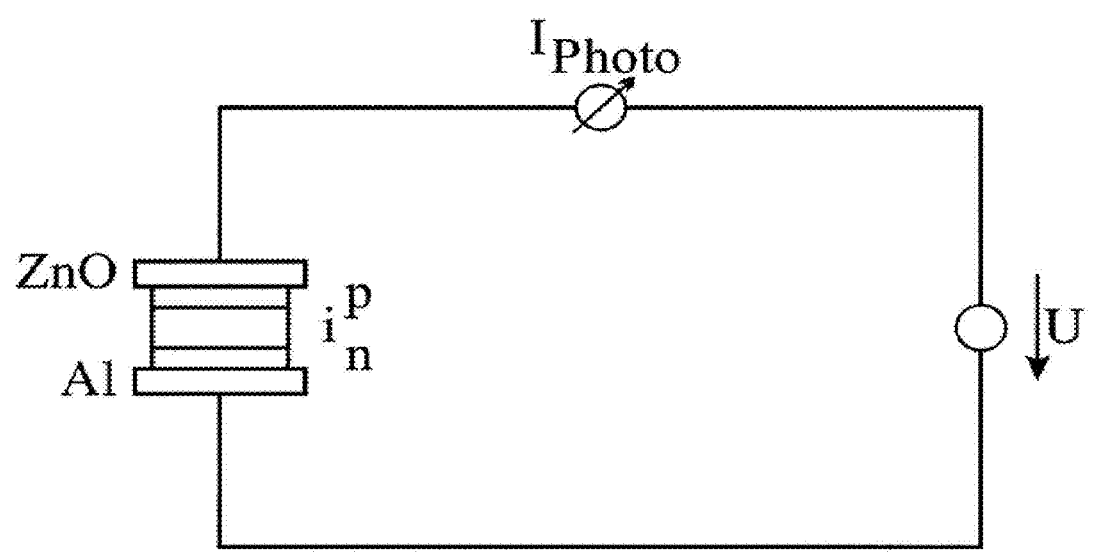
FIG. 6 schematically shows an arrangement for actuating a support according to the invention.

The invention claimed is:

1. A method of analyzing molecular interactions on and/or in a thin layer on a support, comprising the steps of
    illuminating the thin layer using electromagnetic radiation from at least one radiation source,
    detecting radiation reflected on outer faces of the thin layer by at least one optoelectronic sensor that converts the radiation detected into a frequency and intensity dependent photocurrent,
    applying a reading voltage to the optoelectronic sensor for measuring the photocurrent, and
    varying the spectral sensitivity of the optoelectronic sensor by changing the reading voltage such that a substantially constant photocurrent is obtained.

2. The method according to claim 1, wherein parameters are derived from the reading voltage that characterize the interactions to be analyzed on or in the thin layer.

3. The method according to claim 1 wherein the thin layer on the support is turned away from the incident radiation.

4. The method according to claim 1 wherein the molecular interactions to be analyzed are physical, chemical, or biochemical reactions, detection, binding, or agglomeration events.

5. The method according to claim 1 wherein the thin layer is illuminated with electromagnetic radiation having a spectral bandwidth of between 5 nm and 50 nm.

6. The method according to claim 1 wherein the optoelectronic sensor comprises a photodiode of a p-i-n, a p-n, or a n-i-p-i-n type, or a Schottky diode.

7. The method of analyzing molecular interactions on or in a thin layer according to claim 1 wherein the reflected radiation part is detected using an optoelectronic sensor that is a sensor layer in the support.

8. The method according to claim 1 wherein the wavelength of the electromagnetic radiation is varied during illumination, in particular by actuation of at least two different spectrally overlapping radiation sources in opposite directions.

9. The method according to claim 8, wherein the variation of the wavelength of the electromagnetic radiation is carried out synchronously or oppositely to the change of the reading voltage with regard to the change of the photocurrent resulting from it.

10. A support for a thin layer for analyzing molecular interactions on or in the thin layer, in particular in a method according to claim 1, wherein the support has multiple layers, in the order of a protective layer of silicon dioxide, a highly refracting layer of tantalum pentoxide or niobium pentoxide, and a substrate of glass, plastic, or metal on which the at least one sensor layer having optoelectronic properties is provided.

11. The support according to claim 10, wherein the at least one sensor layer has at least one amorphous, nanocrystalline, or polycrystalline, in particular silicon-based semiconductor material having optoelectronic properties, the at least one sensor layer comprising a preferably continuous layer of the at least one semiconductor material or at least one layer subdivided into sections from the at least one semiconductor material.

12. The support according to claim 11, wherein the at least one, preferably continuous or subdivided layer of the at least one semiconductor material is a p-i-n, a p-n, or a n-i-p-i-n type, or a Schottky diode.

13. The support according to claim 11 wherein the at least one, layer of the at least one semiconductor material has a sequence of sublayers comprising a varying optical bandgap and having a layer sequence of $p\text{-}i_1\text{-}i_2\text{-}n$, $p\text{-}i_1\text{-}i_2\text{-}i_3\text{-}n$, $n\text{-}i_1\text{-}i_2\text{-}p$, or $n\text{-}i_1\text{-}p\text{-}i_2\text{-}i_3\text{-}p$.

14. The support according to claim 13, wherein at least one of the sublayers is doped with carbon or germanium.

15. The support according to claim 11 wherein the at least one layer of the at least one semiconductor material has a sequence of sublayers of:
- a p-conducting Si:H layer
- a self-conducting Si:H layer
- a self-conducting Si:H layer
- a n-conducting Si:H layer where Si:H is a thin layer semiconductor on the basis of silicon that is amorphous or crystalline, or undoped or doped or not blended, or blended with carbon, nitrogen, or germanium.

16. The support according to claim 10 wherein the at least one sensor layer has at least one contact layer that preferably directly adjoins the at least one layer of the at least one semiconductor material.

17. The support according to claim 16, wherein the at least one contact layer consists of ZnO, ITO (indium tin oxide) or of metal.

18. The support according to claims 16 wherein the at least one sensor layer has a contact layer and a layer subdivided into sections from the at least one semiconductor material directing adjoining it, the contact layer overlapping the adjoining layer subdivided into sections on at least one side.

19. The support according to claim 16 wherein the at least one sensor layer has a layer sequence of:
- a contact layer, preferably of zinc oxide,
- a preferably continuous or subdivided layer of the at least one semiconductor material having optoelectronic properties,
- a metal contact layer, preferably of aluminum.

* * * * *